United States Patent [19]
Penticoff et al.

[11] Patent Number: 5,078,888
[45] Date of Patent: Jan. 7, 1992

[54] METHOD FOR PROCESSING AQUEOUS FERMENTATION BROTHS

[75] Inventors: Amy M. Penticoff; John D. Lyon, both of Midland, Mich.

[73] Assignee: Dow Corning Corporation, Midland, Mich.

[21] Appl. No.: 680,482

[22] Filed: Apr. 4, 1991

Related U.S. Application Data

[62] Division of Ser. No. 333,677, Apr. 6, 1989, Pat. No. 5,024,937.

[51] Int. Cl.$^5$ .............................................. B01D 61/16
[52] U.S. Cl. ...................................... 210/639; 210/651
[58] Field of Search ...................... 210/639, 651, 631; 435/41, 243, 246, 812, 942

[56] References Cited

U.S. PATENT DOCUMENTS

| | | | |
|---|---|---|---|
| 3,159,585 | 12/1964 | Evans | 252/316 |
| 3,779,942 | 12/1973 | Bolles | 252/316 |
| 3,971,852 | 7/1976 | Brenner | 426/103 |
| 4,481,157 | 11/1984 | Morishita | 264/4.1 |
| 4,732,917 | 3/1988 | Shah | 514/781 |
| 4,859,377 | 8/1989 | Shasha et al. | 435/178 |
| 4,888,140 | 12/1989 | Schlameus et al. | 264/4.4 |
| 4,931,397 | 6/1990 | Montgomery | 435/246 |
| 4,939,087 | 7/1990 | Van Wie et al. | 435/243 |

FOREIGN PATENT DOCUMENTS

| | | |
|---|---|---|
| 97867 | 12/1983 | European Pat. Off. . |
| 0171457 | 4/1986 | European Pat. Off. . |
| 1554642 | 12/1967 | France . |
| WO8605411 | 9/1986 | PCT Int'l Appl. . |
| 892787 | 3/1962 | United Kingdom . |
| 1154256 | 6/1969 | United Kingdom . |
| 2180254 | 3/1987 | United Kingdom . |

*Primary Examiner*—Frank Spear
*Attorney, Agent, or Firm*—Jim L. DeCesare

[57] ABSTRACT

A method for processing aqueous fermentation broths in a bioreactor vessel, in which a foam inhibitor is added to the fermentation broth in the bioreactor vessel in order to prevent the accumulation and buildup of foam in the bioreactor vessel caused by oxygen sparging of the fermentation broth contained therein. The aqueous fermentation broth processed in the bioreactor vessel is conveyed as a feed solution to an ultrafiltration system including a membrane for concentrating the aqueous fermentation broth. The ultrafiltration system is typically located downstream of the bioreactor vessel. The improvement involves reducing the amount of fouling of the membrane in the ultrafiltration system by adding to the aqueous fermentation broth in the bioreactor vessel as the foam inhibitor, an antifoam which is an oil based liquid in the form of droplets, the droplets of the oil based liquid antifoam being dispersed, encased, entrapped, and imbedded, within solid particles of a water soluble encapsulating material.

6 Claims, No Drawings

METHOD FOR PROCESSING AQUEOUS FERMENTATION BROTHS

This is a divisional of copending application Ser. No. 07/333677 filed on 4/6/89, now U.S. Pat. No. 5,024,937.

BACKGROUND OF THE INVENTION

This invention relates to an improved process for treating fermentation broths in which a solid particulate form of encapsulated antifoam is employed in a bioreactor vessel in order that fouling be reduced in ultrafiltration equipment employed downstream of the bioreactor vessel during concentration of the broth.

Fermentation processing involves organisms such as bacteria, yeast, and fungus, in a culture medium of a broth including starch, glucose, oxygen, and various proteins. The aqueous broth is allowed to ferment for a number of days, and as the broth is fermenting, the broth is supplied with a constant amount of oxygen in order to increase the rate of aerobic conversion. As a result of such oxygen sparging, and because of the presence of surface active proteins, a substantial amount of foam is produced in the bioreactor vessel. It has therefore been conventional practice to add a foam inhibitor to the broth in order to reduce the accumulation of foam. Traditionally, such foam inhibitors have been in the form of emulsions including droplets of oil dispersed in water. Such emulsion type antifoam formulations have necessarily included surfactants, coagulants, and gelatinous thickeners, for the purpose of stabilizing these antifoam formulations.

Following completion of the microbial activity in the bioreactor, it is necessary to process the fermentation broth by concentrating the broth in order to separate desired products from the impurities contained in the broth. This processing is typically conducted by passing the fermentation broth from the bioreactor to a filtration unit located downstream of the bioreactor. The filtration systems employed are ultrafiltration units employing membranes. In these separation units, there is generated a high pressure bulk flow of broth across hydrophobic membranes having pore sizes ranging from 0.01 to 1.0 micron. The broth passes through the membrane, while the impurities sought to be separated are retarded by the membrane. These impurities constitute, for example, cells, proteins, and bacteria. It has been found that such membranes are highly sensitive to fouling and clogging, with the result that the filtration rate, expressed as flux through the membrane, is inhibited; the product yield is reduced; and there is a corresponding reduction in the life-span of the membrane itself. One contributing factor to membrane fouling, clogging, and filtration rate inhibition, is believed to be the presence in the antifoam emulsion of the various surfactants, coagulants, and thickeners, used to stabilize emulsion type antifoams. These surfactants, coagulants, and thickeners, form a gel layer at the interface of the membrane and the aqueous phase, and the gel layer clings to the surface of the membrane, inhibiting the filtration rate of the effluent therethrough.

Thus, it should be apparent that there exists a need for an antifoam formulation which will effectively inhibit the formation of foam in the fermentation broth in the bioreactor, and which will also allow high efficiency filtration rates through the membrane, and without the formation of flux inhibiting gel layers prone to foul the membrane and reduce its efficiency.

Encapsulated antifoams are not new, nor is the encapsulation of antifoams in water soluble materials new or novel. For example, it has recently been reported that a new process for encapsulating liquids or solids in a cornstarch matrix for slow release has been developed by the USDA Northern Regional Research Center. The matrix consists of a compound produced from amylose and amylopectin. In order to encapsulate a herbicide, for example, cornstarch is cooked in a jet of steam to gelatinize the starch. The herbicide, insect lure, plant growth regulator, fertilizer, medicine, flavoring, coloring, or vitamin, is mixed in; dried; and the mixture may be crumbled or ground to granules or particles, respectively. In United Kingdom Published Unexamined Application No. 2180254, filed Sept. 10, 1986, and published Mar. 25, 1987, a sugar such as sucrose is used in a detergent composition but acts, rather than an encapsulant, to increase the dispersibility of the detergent. In European Published Unexamined Application No. 0171457, filed Aug. 17, 1984, published Feb. 19, 1986, particles of sugar such as lactose are embedded in a semi-permeable membrane and then dissolved, releasing water soluble actives.

In U.S. Pat. No. 3,159,585, issued Dec. 1, 1964, various oils such as vegetable fats are encapsulated with dextrins. Sugar in the form of mixtures of mannitol, sorbitol, and refined cane sugar, are used to encapsulate mineral oil in U.S. Pat. No. 3,779,942, issued Dec. 18, 1973. Fragrance oils, spice oils, perfume oils, and fruit flavors, are taught in U.S. Pat. No. 3,971,852, issued July 27, 1976, to be encapsulated in a mixture of dextrin and a sugar such as sucrose, fructose, and glucose. In U.S. Pat. No. 4,481,157, issued Nov. 6, 1984, a mixture of gelatin, sorbitol, water, and a coagulant, such as a liquid paraffin, is used to encapsulate vegetable oil. A bulk laxative containing methylcellulose particulates encapsulated in sucrose is disclosed in U.S. Pat. No. 4,732,917, issued Mar. 22, 1988.

A silicone antifoam formulation is disclosed in United Kingdom Patent No. 892,787, granted Mar. 28, 1962, and in which an organosiloxane emulsion including fume silica, is spray dried along with methylcellulose in order to form encapsulated antifoam particles. Other encapsulating materials are disclosed to be starch, gelatin, albumen, gum acacia, locust bean gum, carrageena, polyvinyl alcohol, polyethylene glycol, and guar gum.

However, all of the foregoing references require the presence of one or more of a surfactant, coagulant, thickener, or additive, in order to stabilize the system. In addition, none relate specifically to environments including ultrafiltration equipment or membrane separators, nor do the references relate to fluid treatment systems such as fermentation processes requiring such ultrafiltration equipment or membrane separators.

There is described in PCT International Publication No. WO 86/05411, published Sept. 25, 1986, an ultrafiltration system that employs a silicone alkylene oxide copolymer as a foam inhibitor for the fluids processed therein. This antifoam material is allegedly does not permanently foul the membrane, in comparison to conventional antifoam formulations containing additives such as emulsigying agents. It is noted, however, that in the event the membrane does become fouled, that the fouling process can be reversed by cleaning the membrane using conventional techniques such as flushing the membrane with cold water or with a mild bleach solution. The silicone alkylene oxide copolymeric antifoam material of the PCT International Publication is also disclosed to be operable in functioning as a foam inhibitor in the absence of emulsifiers, solvents, and finely divided insoluble matter.

In accordance with the present invention, a novel alternative foam inhibitor is provided, which foam inhibitor is effective for use, for example, in methods for processing aqueous fermentation broths in a bioreactor vessel, in which the broth is conveyed downstream as a feed solution to an ultrafiltration system including a membrane for concentrating the aqueous fermentation broth. The foam inhibitor is in the form of an oil based liquid in the form of droplets, the droplets of the oil based liquid antifoam being dispersed, encased, entrapped, and imbedded, within solid particles of a water soluble encapsulating material. The encapsulated particulate antifoam is free of additives known to inhibit the filtration rate through the membrane, such as surfactants, coagulants, and thickeners. When added to the fermentation broth, the bland encapsulating material of the present invention, dissolves and releases the additive free active antifoam ingredient into the aqueous phase in the bioreactor vessel.

Unlike the silicone alkylene oxide copolymer of the PCT International Publication referred to previously, the antifoams of the present invention meet the requirements of and are permissible in most foods, as established under rulings of the United States Food and Drug Administration. Further, the materials of the present invention are in an otherwise solid particulate form, rendering them capable of a programmed form of release of the antifoam encapsulated therein, in contrast to the bulk fluids of the PCT International Publication.

SUMMARY OF THE INVENTION

This invention relates to a method for processing aqueous solutions in a treating vessel, in which a foam inhibitor is added to the treating vessel in order to prevent the accumulation and buildup of foam therein, and in which the aqueous solution processed in the treating vessel is conveyed as a feed solution to an ultrafiltration system including a membrane. The ultrafiltration system is typically located downstream of the treating vessel, but the system can also constitute part of the recirculation process in certain instances as well. The improvement involves employing as the foam inhibitor in the treating vessel, an antifoam which is an oil based liquid in the form of droplets. The droplets of the oil based liquid antifoam are dispersed, encased, entrapped, and imbedded, within solid particles of a water soluble encapsulating material.

The invention is also directed to a method for processing aqueous fermentation broths in a bioreactor vessel, in which a foam inhibitor is added to the fermentation broth in the bioreactor vessel in order to prevent the accumulation and buildup of foam in the bioreactor vessel, caused by oxygen sparging of the fermentation broth contained therein. The aqueous fermentation broth processed in the bioreactor vessel is conveyed as a feed solution to an ultrafiltration system, including a membrane for concentrating the aqueous fermentation broth. The ultrafiltration system is typically located downstream of the bioreactor vessel. The improvement in this process involves reducing the amount of fouling of the membrane in the ultrafiltration system by adding to the aqueous fermentation broth in the bioreactor vessel as the foam inhibitor, an antifoam which is an oil based liquid in the form of droplets. The droplets of the oil based liquid antifoam are dispersed, encased, entrapped, and imbedded, within solid particles of a water soluble encapsulating material.

In some particular and preferred embodiments of the present invention, the oil based liquid antifoam is selected from the group consisting of silicone oils, vegetable oils, and mineral oils. The water soluble encapsulating material is selected from the group consisting of sugars and hydrolysis products of starch, and can include such materials as maltodextrin, glucose, maltose, sucrose, fructose, xylose, and lactose. The antifoam should be otherwise free of surfactants, thickeners, and coagulants, or other additives which tend to clog the membrane.

These and other features, objects, and advantages, of the present invention will become more apparent when considered in light of the following detailed description thereof.

DETAILED DESCRIPTION OF THE INVENTION

Ultrafiltration is a separation technique in which a liquid including small dissolved molecules is forced through a porous membrane. Large dissolved molecules, colloids, and suspended solids which do not migrate through the membrane pores are retained. The membranes are typically constructed of polymeric materials such as cellulose acetates, polyamides, polysulfones, vinyl chloride-acrylonitrile copolymers, and polyvinylidene fluoride. The membrane may be employed in the form of a flat sheet; a parallel leaf cartridge including several flat plates each with a membrane on both sides; a plate and frame assembly; a spirally wound cartridge of a pair of membrane sheets separated by a flexible porous support; supported tubes; and pleated sheets. Such ultrafiltration equipment is adapted to a wide variety of processing applications including, for example, protein recovery; the manufacture of cheese and yogurt; the concentration of oil and water emulsions; lanolin recovery; the concentration and purification of enzymes; antibiotic manufacture; alcohol fermentation; sewage treatment; and blood fractionation and purification. One distinct disadvantage of ultrafiltration is that retained materials which do not pass through the pores of the membrane tend to collect on the surface of the membrane, forming a gel layer which limits the filtration rate expressed as flux. In order to minimize the thickness of the gel layer, such systems are designed so that the flow of influent sweeps across the membrane surface. Material is recirculated in order to maintain a sufficient velocity across the surface of the membrane.

Often ultrafiltration units are used in processes wherein the ultrafiltration equipment is deployed at a location downstream of a treatment type vessel. These vessels frequently require the addition of foam inhibiting agents during the treatment process. While such foam inhibiting agents are effective in preventing the buildup of foam in the treatment vessel; the surfactants, coagulants, and thickeners, used to stabilize such antifoam agents, are one of the major contributors in the maintenance of the gel layer.

In an effort to minimize the contribution of materials to the gel layer formed at the surface of the membrane, the antifoam formulation of the present invention excludes surfactants, coagulants, and thickeners, or other additives, typically found in foam inhibiting agents. Exemplary of materials sought to be excluded from the compositions of the present invention are common surfactants such as glycerol monostearate, polyoxyethylene sorbitan tristearate, and polyoxyethylene monostearate; and thickeners such as xanthan gums, hydroxypropyl methylcellulose, and carboxy methylcellulose. This exclusion of additive materials is accomplished by encapsulating the antifoam active ingredient in a water soluble material in the form of a solid particulate. In this solid particulate encapsulated form, the antifoam active ingredient is otherwise preserved in a stabilized fashion, and can be stored for extended periods of time prior to being used. Upon addition of the particles of encapsulated antifoam to an aqueous system, the water soluble material is dissolved, releasing the antifoam active ingredient into the aqueous phase in order to perform its foam inhibiting function.

The water soluble material used to encapsulate the antifoam active ingredient in accordance with the present invention, can be either a hydrolysis product of starch such as maltodextrin, or a sugar such as glucose, maltose, sucrose, fructose, xylose, and lactose. Maltodextrin is the preferred encapsulating material because of its bland characteristics. The antifoam active may contain a finely divided particulate filler, typically, silica, in addition to the fluid component of the antifoam. The fluid component of the antifoam active ingredient may be one or more of, or mixtures of, oil based liquids such as mineral oils and vegetable oils. Preferred vegetable oils are soybean oil, peanut oil, corn oil, rapeseed oil, coconut oil, palm oil, olive oil, sesame oil, cottonseed oil, sunflower oil, and safflower oil. There may also be used, in addition to mineral oils and vegetable oils, an oil based liquid of a silicone.

The term silicone denotes a polymer of the formula

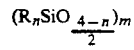

wherein n is an integer between zero and three, and m is two or more. The simplest silicone materials are the polydimethylsiloxanes. Polydimethylsiloxanes have the structure

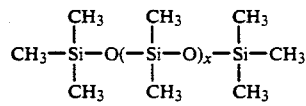

where x is an integer of from one to about one hundred thousand. The repeating unit of the polymer

is the dimethylsiloxane unit. The terminal unit (Me3SiO) is the trimethylsiloxy group. At low molecular weights, silicones are fluids, and at high molecular weights, they are gums which may be cross-linked to form elastomeric products. The methyl group in a silicone may be substituted by a variety of other substituents including for example, phenyl, vinyl, and hydrogen. Conventional silicones are the trimethylsiloxy terminated polydimethylsiloxanes. Such materials are available in viscosities ranging from 0.65 to 2,500,000 centistokes. Substituents on the silicon consist of methyl groups or oxygen. Termination of the polymer chain prevents viscosity change and other alterations of the physical properties of the silicone polymeric materials.

The polydimethylsiloxanes exhibit characteristic properties of low viscosity change with temperature; thermal stability; oxidative stability; chemical inertness; non-flammability; low surface tension; high compressibility; shear stability; and dielectric stability. In resin forming polysiloxanes, some of the methyl groups are hydrolyzable and permit the formation of Si—O—Si cross-links upon heating in the presence of a catalyst, but in the organosilicon fluids and oils, substantially all of the methyl groups are non-hydrolyzable and the fluid is heat stable.

The polydimethylsiloxane fluid used herein as the antifoam agent is a high molecular weight polymer having a molecular weight in the range from about 200 to about 200,000, and has a viscosity in the range from about 20 to 2,000,000 centistokes, preferably from about 500 to 50,000 centistokes, more preferably about 550 to 1,200 centistokes at 25° C. The siloxane polymer is generally end-blocked either with trimethylsilyl or hydroxyl groups but other end-blocking groups are also suitable. The polymer can be prepared by various techniques such as the hydrolysis and subsequent condensation of dimethyldihalosilanes, or by the cracking and subsequent condensation of dimethylcyclosiloxanes.

The polydimethylsiloxane fluid antifoam agent can be present in combination with particulate silica. Such combinations of silicone and silica can be prepared by affixing the silicone to the surface of silica, for example, by means of the catalytic reaction disclosed in U.S. Pat. No. 3,235,509. Foam regulating agents comprising mixtures of silicone and silica prepared in this manner preferably comprise silicone and silica in a silicone:silica ratio of from 20:1 to 200:1, preferably about 25:1 to about 100:1. The silica can be chemically and/or physically bound to the silicone in an amount which is preferably about 0.5% to 5% by weight, based on the silicone. The particle size of the silica employed in such silica/silicone foam regulating agents is finely divided and should preferably be not more than 100 microns, preferably from 2 microns to 20 microns.

Alternatively, silicone and silica can be prepared for use in the antifoam agent by admixing a silicone fluid of the type herein disclosed with a hydrophobic silica having a particle size and surface area in the range disclosed above. Any of several known methods may be used for making a hydrophobic silica which can be employed herein in combination with a silicone as the foam regulating agent. For example, a fumed silica can be reacted with a trialkyl chlorosilane (i.e., "silanated") to affix hydrophobic trialkylsilane groups on the surface of the silica. In a preferred and well known process, fumed silica is contacted with trimethylchlorosilane. A preferred material comprises a hydrophobic silanated, most preferably trimethylsilanated, silica, intimately admixed with a dimethyl silicone fluid having a molecular weight in the range of from about 200 to about 200,000, at a weight ratio of silicone to silanated silica of from about 20:1 to about 200:1, preferably from about 20:1 to about 100:1.

Yet another type of material suitable herein as the polydimethylsiloxane fluid antifoam comprises polydimethylsiloxane fluid, a silicone resin and silica. The silicone "resins" used in such compositions can be any alkylated silicone resins, but are usually those prepared from methylsilanes. Silicone resins are commonly described as "three-dimensional" polymers arising from the hydrolysis of alkyl trichlorosilanes, whereas the silicone fluids are "two-dimensional" polymers prepared from the hydrolysis of dichlorosilanes. The silica components of such compositions are microporous materials such as fumed silica aerogels and xerogels having particle sizes and surface areas herein-above disclosed.

The mixed polydimethylsiloxane fluid/silicone resin/silica materials useful in the present compositions as antifoam agent can be prepared in the manner disclosed in U.S. Pat. No. 3,455,839. Preferred materials of this type comprise:

(a) from about 10 parts to about 100 parts by weight of a polydimethylsiloxane fluid having a viscosity in the range from 20 to 30,000 mm/s at 25° C.:

(b) 5 to 50 parts by weight of a siloxane resin composed of $(CH_3)_3SiO_{\frac{1}{2}}$ units and $SiO_2$ units in which the ratio of the $(CH_3)_3 SiO_{\frac{1}{2}}$ units to the $SiO_2$ units is within the range of from 0.6/1 to 1.2/1: and (c) 0.5 to 5 parts by weight of a silica aerogel, precipitated silica, or hydrophobic silica. Such mixtures can also be sorbed onto and into a water-soluble solid.

Essentially, the antifoam of the present invention includes silica particles, one of an oil of mineral oil, vegetable oil, and silicone oil, encapsulated in a water soluble solid such as sugar or a hydrolysis product of starch. The encapsulated antifoam has been found to inhibit foaming in aqueous yeast broths of Saccharomyces cerevisiae, and at the same time, the encapsulated antifoams of the present invention do not cause severe irreversible fouling of the membranes akin to the antifoam formulations of the prior art. Several examples, testing procedures, and tables, are shown hereinafter in order to more completely illustrate the concepts of the present invention. Percentages of materials expressed in the examples, tests, and tables, are intended as weight percentages, unless otherwise specified.

The antifoam can be delivered in a dry solid capsule or powder form and dissolved to release the antifoam. The encapsulation is achieved by dispersing the oil and silica into a heated sugar and water solution. The sugar melt is cooled and solidified entrapping the defoaming active moiety. The solid is broken into various particle sizes. Alternatively, the melt can be dried and formed into microparticles by spray drying. The antifoam can be used in fermentation broths to inhibit foaming without causing fouling of the ultrafilters used in enzyme concentration downstream of the bioreactor. Contact with an aqueous solution causes dissolution of the sugar encapsulator releasing the antifoam.

EXAMPLE I

A solution of 30-35% maltodextrin and 30-35% water was heated with stirring until the maltodextrin melted and dissolved in water. A solution of 3-10% vegetable oil and hydrophobic silica was added. The mixture was heated and stirred until the oil and silica were dispersed. The mixture was poured onto a silicon-treated paper and allowed to dry overnight. The hardened crystalline material was broken into various particle sizes.

EXAMPLE II

A solution of 30-35% maltodextrin and 30-35% water was heated with stirring until the maltodextrin melted and dissolved in water. A solution of 3-10% mineral oil and hydrophobic silica was added. The mixture was heated and stirred until the oil and silica were dispersed. The water was removed via spray drying, and the powder and granules were collected.

Table I shows compositions A-D prepared in accordance with Examples I and II.

TABLE I

|  | A | B | C | D |
|---|---|---|---|---|
| Maltodextrin* | 63.63% | 60.00% | 60.00% | 65.57% |
| Water | 30.91% | 35.00% | 5.60% | 30.16% |
| Soybean oil | 4.55% | — | — | — |
| Mineral oil | — | 4.00% | 4.00% | 3.94% |
| Hydrophobic silica | .91% | 1.00% | 0.40% | 0.33% |

* = Manufactured by A.E. Staley Mfg. Co., Decatur, Illinois, and sold under the Trademark STAR-DRI ®.

The defoaming efficiency of compositions A-D prepared above in Examples I and II, and shown in Table I, was determined by using a one thousand milliliter graduated cylinder, equipped with a gas dispersion tube terminating in a stone sparger. Two hundred milliliter samples were loaded into the cylinder and an air flow rate of five hundred milliliters per minute was used to sparge the contents. The contents were sparged with air continuously while at the same time measuring the foam height at each fifteen second interval. The control sample included two hundred milliliters of deionized water containing three percent by weight of S. cerevisiae, but containing no antifoam agent. The yeast S. cerevisiae was added to simulate a fermentation broth. Test samples including twenty-five parts per million of each of antifoam compositions A-D, were prepared in two hundred milliliters of deionized water containing three percent by weight of S. cerevisiae, and sparged as indicated above. The results of such tests of the defoaming ability of the encapsulated antifoams of the present invention can be seen in Table II.

TABLE II

| Time (sec.) | Foam Height (ml.) | | | | | |
|---|---|---|---|---|---|---|
|  | Control | X* | A | B | C | D |
| 15 | 500 | 400 | 400 | 300 | 340 | 450 |
| 30 | 670 | 500 | 440 | 330 | 320 | 450 |
| 45 | 760 | 650 | 400 | 350 | 310 | 470 |
| 60 | 770 | 650 | 350 | 350 | 310 | 400 |
| 75 | 750 | 800 | 350 | 350 | 300 | 350 |
| 300 | — | >1000 | 300 | 350 | 300 | 300 |

* = Polyglycol based antifoam for comparison.

In Examples III and IV set forth below, additional encapsulated antifoams were prepared including silicone based oils. Compositions E-G prepared in accordance with Examples III and IV are shown in Table III. In Table III, compound Y is a polydimethylsiloxane fluid having a viscosity of about 550 centipoises measured at twenty-five degrees Centigrade, and including a silica filler. Compound Z is also a silica filled polydimethylsiloxane fluid but of a viscosity of about 1200 centipoises. The defoaming efficiency of these encapsulated silicone antifoam formulations E-G was tested in accordance with the procedure outlined hereinbefore, and the results of such defoaming tests is shown in Table IV.

EXAMPLE III

A solution of 55-95% maltodextrin, 5-30% silicone antifoam compound and 1-35% water was heated with stirring until the maltodextrin melted and dissolved in water. The solution was poured onto silicon-treated paper and allowed to dry overnight. The hardened crystalline material was broken into various particle sizes.

EXAMPLE IV

A solution of 55-95% maltodextrin and 30-35% water was heated with stirring until the maltodextrin melted and dissolved in water silicone antifoam compound, 3-10% by weight, was added. The mixture was heated and stirred until the compound was dispersed. The water was removed via spray drying, and the powder and granules were collected.

TABLE III

|  | E | F | G |
|---|---|---|---|
| Maltodextrin* | 60.0% | — | 57.14% |
| Maltodextrin** | — | 62.5% | — |
| Compound Y | 5.0% | 20.83% | — |
| Compound Z | — | — | 14.29% |
| Water | 35.0% | 16.67% | 28.57% |

\* = See Table I.
\*\* = Sold under the Trademark MALTRIN ®.

TABLE IV

| Time (sec.) | Foam Height (ml.) | | | |
|---|---|---|---|---|
|  | Control | E | F | G |
| 15 | 500 | 300 | 450 | 325 |
| 30 | 670 | 300 | 550 | 400 |
| 45 | 760 | 350 | 600 | 450 |
| 60 | 770 | 350 | 600 | 450 |
| 75 | 750 | 240 | 600 | 450 |

It has been found in accordance with the teaching of the present invention, that any membrane fouling which may occur, is reversible, and that the ultrafiltration membrane surface can be cleaned. Such cleaning may be accomplished by passing through the membrane about ten liters of 0.1M sodium hydroxide solution, or about ten liters of 0.5 weight percent of TERGAZYME ® enzymatic cleaner, for fifteen minutes. Two ten liter volumes of clear deionized water are flushed through the system following this treatment.

While particular weight percentages of ingredients of the encapsulated antifoams are set forth in Examples I-IV, the compositions of the present invention are not limited to such amounts, and the various ingredients may be employed in other and varying percentages. For example, maltodextrin may be present and can constitute from about 55-95 weight percent of the encapsulated antifoam formulation. The silica filler can be present and may constitute from about one to about nine weight percent. The siloxane fluid is preferably employed in the amount of from about three to about twenty weight percent; while vegetable oils and mineral oils can comprise from about five to about thirty percent by weight.

In the following table, data are set forth indicating results obtained from tests conducted for the purpose of determining fouling and clogging which may occur as a result of the presence of several antifoam formulations in a solution of deionized water containing about one hundred parts per million of antifoam formulation. A membrane constructed of a polysulfone material in sheet form and having an approximate molecular weight cut off of about 25,000 was employed. The table expresses the percent relative flux obtained during such tests as a function of the time in minutes which elapsed, in order for fifty milliliters of filtrate to be collected through the membrane. The flux following cleaning of the membrane, is also reflected in Table V. As noted previously, flux is an expression of filtration rate, and the most ideal flux is related to the value obtained when pure water, free of antifoam agent, is passed through the membrane. Solutions containing encapsulated antifoam formulations prepared in accordance with the present invention, as well as comparitive antifoam formulations, are shown in Table V.

TABLE V

| Filtration Time (min.) | % RELATIVE FLUX* | | | |
|---|---|---|---|---|
|  | Control (Water) | A | X*** | F |
| 0 | 100 | 100 | 100 | 100 |
| 30 | 91.0 | 87.6 | 23.7 | 80.4 |
| 60 | 91.0 | 87.6 | 23.7 | 74.3 |
| 90 | 88.8 | 87.6 | 23.7 | 75.4 |
| 120 | 82.1 | 82.3 | 23.2 | 69.0 |
| Flux after cleaning** | — | — | 73.1 | 87.5 |

*The initial permeate flux of deionized water was measured and considered 100%. The permeate flux was measured at 30 minute intervals after addition of antifoam and compared to the initial flux.
**The membranes were treated with TERGAZYME ®, an enzymatic cleaner, for ten minutes, rinsed with deionized water and the permeate flux remeasured.
***Polyglycol based antifoam for comparison.

It will be apparent from the foregoing that many other variations and modifications may be made in the structures, compounds, compositions, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. In a method for processing aqueous solutions in a treating vessel, in which a foam inhibitor is added to the treating vessel in order to prevent the accumulation and buildup of foam therein, and in which the aqueous solution processed in the treating vessel is conveyed as a feed solution to an ultrafiltration system including a membrane, the ultrafiltration system being located downstream of the treating vessel, the improvement comprising employing as the foam inhibitor in the treating vessel, an antifoam which is an oil based liquid in the form of droplets, the droplets of the oil based liquid antifoam being dispersed, encased, entrapped, and imbedded, within solid particles of a water soluble encapsulating material.

2. The method of claim 1 wherein the oil based liquid antifoam is selected from the group consisting of silicone oils, vegetable oils, and mineral oils.

3. The method of claim 2 wherein the water soluble encapsulating material is selected from the group consisting of sugars and hydrolysis products of starch.

4. The method of claim 3 wherein the water soluble encapsulating material is maltodextrin.

5. The method of claim 2 wherein the water soluble encapsulating material is selected from the group consisting of maltodextrin, glucose, maltose, sucrose, fructose, xylose, and lactose.

6. The method of claim 1 wherein the antifoam is free of surfactants, thickeners, and coagulants.

* * * * *